United States Patent
Arakawa

(10) Patent No.: US 7,659,512 B2
(45) Date of Patent: Feb. 9, 2010

(54) OIL TYPE DISCRIMINATION METHOD AND OIL TYPE DISCRIMINATOR

(75) Inventor: Satoshi Arakawa, Tokyo (JP)

(73) Assignee: DKK-TOA Corporation, Tokyo (JP)

( * ) Notice: Subject to any disclaimer, the term of this patent is extended or adjusted under 35 U.S.C. 154(b) by 0 days.

(21) Appl. No.: 12/305,448

(22) PCT Filed: Jun. 27, 2007

(86) PCT No.: PCT/JP2007/062904

§ 371 (c)(1),
(2), (4) Date: Dec. 18, 2008

(87) PCT Pub. No.: WO2008/004477

PCT Pub. Date: Jan. 10, 2008

(65) Prior Publication Data

US 2009/0279072 A1     Nov. 12, 2009

(30) Foreign Application Priority Data

Jul. 4, 2006    (JP)    ............................. 2006-184611
Jun. 21, 2007    (JP)    ............................. 2007-163832

(51) Int. Cl.
     *G01N 21/35*      (2006.01)
(52) U.S. Cl. ................................. 250/339.12
(58) Field of Classification Search ................. 250/301, 250/339.12
See application file for complete search history.

(56) References Cited

U.S. PATENT DOCUMENTS 5,349,188 A     9/1994   Maggard
5,672,873 A *   9/1997   Yamazoe ................ 250/339.12
6,140,647 A *   10/2000   Welch et al. ............ 250/339.12

FOREIGN PATENT DOCUMENTS

JP     7-294428 A    11/1995
JP     7-301599 A    11/1995
JP    10-329899 A    12/1998
JP    11-14542 A    1/1999

* cited by examiner

*Primary Examiner*—Constantine Hannaher
(74) *Attorney, Agent, or Firm*—Birch, Stewart, Kolasch & Birch, LLP

(57) ABSTRACT

To provide an oil type discrimination method and an oil type discriminator capable of accurately discriminating a type of oil even when light-shielding components exist in the oil and of preventing in advance erroneous discrimination of a mixture of oil.

There are provided step S1 in which the transmission spectrum of near infrared light is measured, step S2 in which the transmission spectrum is converted into an absorbance spectrum, a first discrimination step S3 in which between gasoline type and non-gasoline type is discriminated by comparing the difference in absorbance between two wavelengths existing in the vicinities of respective attribute wavelengths of predetermined chemical bonds with 0.0, step S4 in which the first derivative spectrum of the absorbance is found, a second discrimination step S5 in which a value, which is obtained by multiplying respective first derivative values of absorbance of at least four wavelengths existing in the vicinities of respective attribute wavelengths of predetermined chemical bonds by respective coefficients and further adding a constant to the sum, is compared with 0.0 and thus between regular gasoline and high-octane gasoline is discriminated, and a third discrimination step S6 in which the difference in absorbance between two wavelengths existing in the vicinities of respective attribute wavelengths of predetermined chemical bonds is compared with 0.0 and thus between kerosene and diesel oil is discriminated.

9 Claims, 6 Drawing Sheets

OIL TYPE DISCRIMINATION METHOD AND OIL TYPE DISCRIMINATOR

BACKGROUND OF THE INVENTION

1. Field of the Invention

The present invention relates to an oil type discrimination method and an oil type discriminator to execute the method used when oils of different types are transported in order or classified and stored in respective tanks, for example, in a pipeline or at an oil tank station. More particularly, the invention relates to an oil type discrimination method and an oil type discriminator that discriminate the type of oil of regular gasoline, high-octane gasoline, kerosene, and diesel oil from each other using near infrared light.

2. Description of the Related Art

As an oil type discrimination method of this kind, a discrimination method that uses sound waves and a discrimination method that uses the absorbance of a specific wavelength of ultraviolet light are known.

However, with the method that uses sound waves, it is difficult to discriminate between regular gasoline and high-octane gasoline, and there is a problem that the dependence of sound speed upon temperature. The method that uses the absorbance of a specific wavelength of ultraviolet light is less versatile because the absorbance of, for example, gasoline, differs from maker to maker and at the same time, a high-voltage power source is necessary as a power source of a light source, and therefore, it is required to install the light source away from a sensor to design for an explosion-proof structure, and thus there is a problem that the size of the discriminator becomes large.

As an oil type discrimination method capable of solving these problems, a method of measuring the absorbance of near infrared light is described in, for example, Japanese Patent Application Laid-open No. H7-294428 (for example, see claims 1 to 3).

In the oil type discrimination method described in Japanese Patent Application Laid-open No. H7-294428, the absorbance or the transmitted light output of an oil is measured using one wavelength or plural wavelengths of light in a near infrared region, and then, the absorbance or the value of transmitted light output obtained using one wavelength and subjected to operation processing, or the absorbance or the value of transmitted light output obtained using two or more wavelengths and subjected to operation processing is compared with their reference value, and thus the type of oil is discriminated.

It is desirable that the one wavelength is set to about 925 to 940 nm or about 1,210 to 1,240 nm, or two wavelengths, that is, a first wavelength of about 930 nm and a second wavelength of about 960 to 1,000 nm, or two wavelengths, that is, a first wavelength of about 1,210 nm and a second wavelength of about 1,150 to 1,200 nm, or two wavelengths, that is, a first wavelength of about 1,220 nm and a second wavelength of about 1,240 to 1,400 nm are used.

With the oil type discrimination method according to Japanese Patent Application Laid-open No. H7-294428, it is possible to discriminate between regular gasoline and high-octane gasoline and there is no influence of temperature, and further a power source and a sensor of small power type can be used, and therefore, an explosion-proof structure can be implemented comparatively easily.

However, with the discrimination method described in Japanese Patent Application Laid-open No. H7-294428, if components that shield transmitted light (hereinafter, "light-shielding components"), such as bubbles, water, and iron powder, exist in an oil, a variation is caused in the light incident to the sensor and there is a problem that the type of oil cannot be accurately discriminated.

On the other hand, in a pipeline or at an oil tank station, when the type of oil to be transported is switched to another, a state is brought about where two types of oils are mixed before and after the switching, and in this case, there is a possibility that the absorbance of the mixed oil closely resembles the absorbance of a single type of oil depending on the types of mixed oils, causing an erroneous discrimination of the type of oil.

SUMMARY OF THE INVENTION

In order to solve the above problems, an object of the present invention is to make it possible to accurately discriminate a type of oil from another even when light-shielding components exist in the oil, and to provide an oil type discrimination method and an oil type discriminator capable of preventing in advance an erroneous discrimination when plural types of oils are mixed.

In order to solve the above problems, a first aspect of the present invention provides an oil type discrimination method, in which a sample, which is an oil to be discriminated from another, is irradiated with near infrared light and a type of oil of the sample is discriminated by measuring absorbance of a specific wavelength of the near infrared light, the method comprising:

a spectrum measurement step of measuring a transmission spectrum of the near infrared light that has transmitted the sample;

a spectrum conversion step of converting the transmission spectrum into an absorbance spectrum;

a first discrimination step of finding a difference in absorbance between two wavelengths existing in the vicinities of respective attribute wavelengths of predetermined chemical bonds and discriminating whether the sample is gasoline type or non-gasoline type by comparing the difference in absorbance with a first reference value;

a first derivative step of converting the absorbance into a first derivative spectrum when the sample is discriminated to be the gasoline type in the first discrimination step;

a second discrimination step of discriminating whether the sample is regular gasoline or high-octane gasoline by comparing a value, which is obtained by multiplying respective first derivative values of absorbance of at least four wavelengths existing in the vicinities of the respective attribute wavelengths of the predetermined chemical bonds by respective coefficients, adding up products, and further adding a constant to a sum, with a second reference; and a third discrimination step of discriminating whether the sample is kerosene or diesel oil by finding the difference in absorbance between two wavelengths existing in the vicinities of the respective attribute wavelengths of the predetermined chemical bonds and comparing the difference in absorbance with a third reference value when the sample is discriminated to be the non-gasoline type in the first discrimination step.

A second aspect of the present invention provides the oil type discrimination method according to the first aspect, wherein the attribute wavelengths in the second discrimination step are 875 nm, 928 nm, and 934 nm or 938 nm.

A third aspect of the present invention provides the oil type discrimination method according to the first aspect, wherein the attribute wavelengths in the second discrimination step are 875 nm, 928 nm, 970 nm, and 934 nm or 938 nm.

A fourth aspect of the present invention provides an oil type discrimination method, in which a sample, which is an oil to be discriminated from another, is irradiated with near infrared light and a type of oil of the sample is discriminated by measuring absorbance of a specific wavelength of the near infrared light, the method comprising:

a spectrum measurement step of measuring a transmission spectrum of the near infrared light that has transmitted the sample;

a spectrum conversion step of converting the transmission spectrum into an absorbance spectrum;

a first discrimination step of finding a difference in absorbance between two wavelengths existing in the vicinities of respective attribute wavelengths of predetermined chemical bonds and discriminating whether the sample is gasoline type or non-gasoline type by comparing the difference in absorbance with a first reference value;

a first derivative step of converting the absorbance into a first derivative spectrum when the sample is discriminated to be the gasoline type in the first discrimination step;

a second discrimination step of discriminating whether the sample is regular gasoline or high-octane gasoline by comparing a value, which is obtained by multiplying respective first derivative values of three wavelengths, that is, two wavelengths existing in the vicinities of the respective attribute wavelengths (an attribute wavelength group) of the predetermined chemical bonds and one wavelength of the attribute wavelength itself (a specific attribute wavelength) of the predetermined chemical bond, by respective coefficients, adding up products, and further adding a constant to a sum, with a second reference; and a third discrimination step of discriminating whether the sample is kerosene or diesel oil by finding the difference in absorbance between two wavelengths existing in the vicinities of the respective attribute wavelengths of the predetermined chemical bonds and comparing the difference in absorbance with a third reference value when the sample is discriminated to be the non-gasoline type in the first discrimination step.

A fifth aspect of the present invention provides the oil type discrimination method according to the fourth aspect, wherein the wavelengths of the attribute wavelength group in the second discrimination step are 875 nm, and 913 nm or 928 nm, and the specific attribute wavelength is 934 nm.

A sixth aspect of the present invention provides the oil type discrimination method according to any one of the first to fifth aspects, wherein prior to the first discrimination step, a mixture determination step of determining whether a deviation of the absorbance spectrum or the transmission spectrum between a previous measurement and a current measurement is smaller than a determination value is provided, and when it is determined that the deviation is smaller than the determination value in the mixture determination step, the sample is regarded to include only one type of oil and a procedure is advanced to processing in the first discrimination step and subsequent steps.

A seventh aspect of the present invention provides an oil type discriminator comprising a detection cell that irradiates a sample, which is an oil to be discriminated, with near infrared light and measures a transmission spectrum of the near infrared light that has transmitted the sample and an oil type discriminator main body that detects absorbance of a specific wavelength from the transmission spectrum and discriminates a type of oil of the sample, wherein the oil type discriminator main body comprises:

a spectrum converting unit that converts the transmission spectrum into an absorbance spectrum;

a first discriminating unit that discriminates whether the sample is gasoline type or non-gasoline type by finding a difference in absorbance between two wavelengths existing in the vicinities of respective attribute wavelengths of predetermined chemical bonds and comparing the difference in absorbance with a first reference value;

a first derivative unit that converts the absorbance of the sample discriminated to be the gasoline type by the first discriminating unit into a first derivative spectrum;

a second discriminating unit that determines whether the sample is regular gasoline or high-octane gasoline by comparing a value including first derivative values of absorbance of at least four wavelengths existing in the vicinities of the respective attribute wavelengths of the predetermined chemical bonds with a second reference value; and a third discriminating unit that finds the difference in absorbance between two wavelengths existing in the vicinities of the respective attribute wavelengths of the predetermined chemical bonds for the sample discriminated to be the non-gasoline type by the first discriminating unit and discriminates whether the sample is kerosene or diesel oil by comparing the difference in absorbance with a third reference value.

An eighth aspect of the present invention provides an oil type discriminator comprising a detection cell that irradiates a sample, which is an oil to be discriminated, with near infrared light and measures a transmission spectrum of the near infrared light that has transmitted the sample and an oil type discriminator main body that detects absorbance of a specific wavelength from the transmission spectrum and discriminates a type of oil of the sample, wherein the oil type discriminator main body comprises:

a spectrum converting unit that converts the transmission spectrum into an absorbance spectrum;

a first discriminating unit that discriminates whether the sample is gasoline type or non-gasoline type by finding a difference in absorbance between two wavelengths existing in the vicinities of the respective attribute wavelengths of the predetermined chemical bonds and comparing the difference in absorbance with a first reference value;

a first derivative unit that converts the absorbance of the sample discriminated to be the gasoline type by the first discriminating unit into a first derivative spectrum;

a second discriminating unit that determines whether the sample is regular gasoline or high-octane gasoline by comparing a value including first derivative values of the absorbance of three wavelengths, that is, two wavelengths existing in the vicinities of the respective attribute wavelengths of the predetermined chemical bonds and one wavelength of the attribute wavelength itself of the predetermined chemical bond with a second reference value; and a third discriminating unit that finds the difference in absorbance between two wavelengths existing in the vicinities of the respective attribute wavelengths of the predetermined chemical bonds for the sample discriminated to be the non-gasoline type by the first discriminating unit and discriminates whether the sample is kerosene or diesel oil by comparing the difference in absorbance with a third reference value.

A ninth aspect of the present invention provides the oil type discriminator according to the seventh or eighth aspects, comprising a mixture determining unit that determines whether deviation of the absorbance spectrum or the transmission spectrum between a previous measurement and a current measurement is smaller than a determination value, wherein processing by the first discriminating unit is executed by determination output from the mixture determining unit.

According to the present invention, it is possible to accurately discriminate between the gasoline type and the non-gasoline type and between kerosene and diesel oil based on the difference in absorbance between two wavelengths existing in the vicinities of respective attribute wavelengths of plural chemical bonds constituting various samples. As for the gasoline type, because regular gasoline is discriminated from high-octane gasoline based on the first derivative values of the absorbance of at least four wavelengths existing in the vicinities of the respective attribute wavelengths, or the first derivative values of the absorbance of three wavelengths, that is, two wavelengths existing respectively in the vicinities of the attribute wavelength group and one wavelength that is the specific attribute wavelength, it is possible to accurately discriminate the type of gasoline from another due to the immutability of the first derivative value even if light-shielding components, such as bubbles, exist in the sample.

Further, by using light in a comparatively short wavelength region of the near infrared region, it is possible to accurately discriminate even when water is included in the sample because the amount of absorption of light by water is small and at the same time, an inexpensive detection cell can be used.

DETAILED DESCRIPTION OF THE PREFERRED EMBODIMENTS

Embodiments of the present invention are explained below with reference to the drawings.

Figure 1:
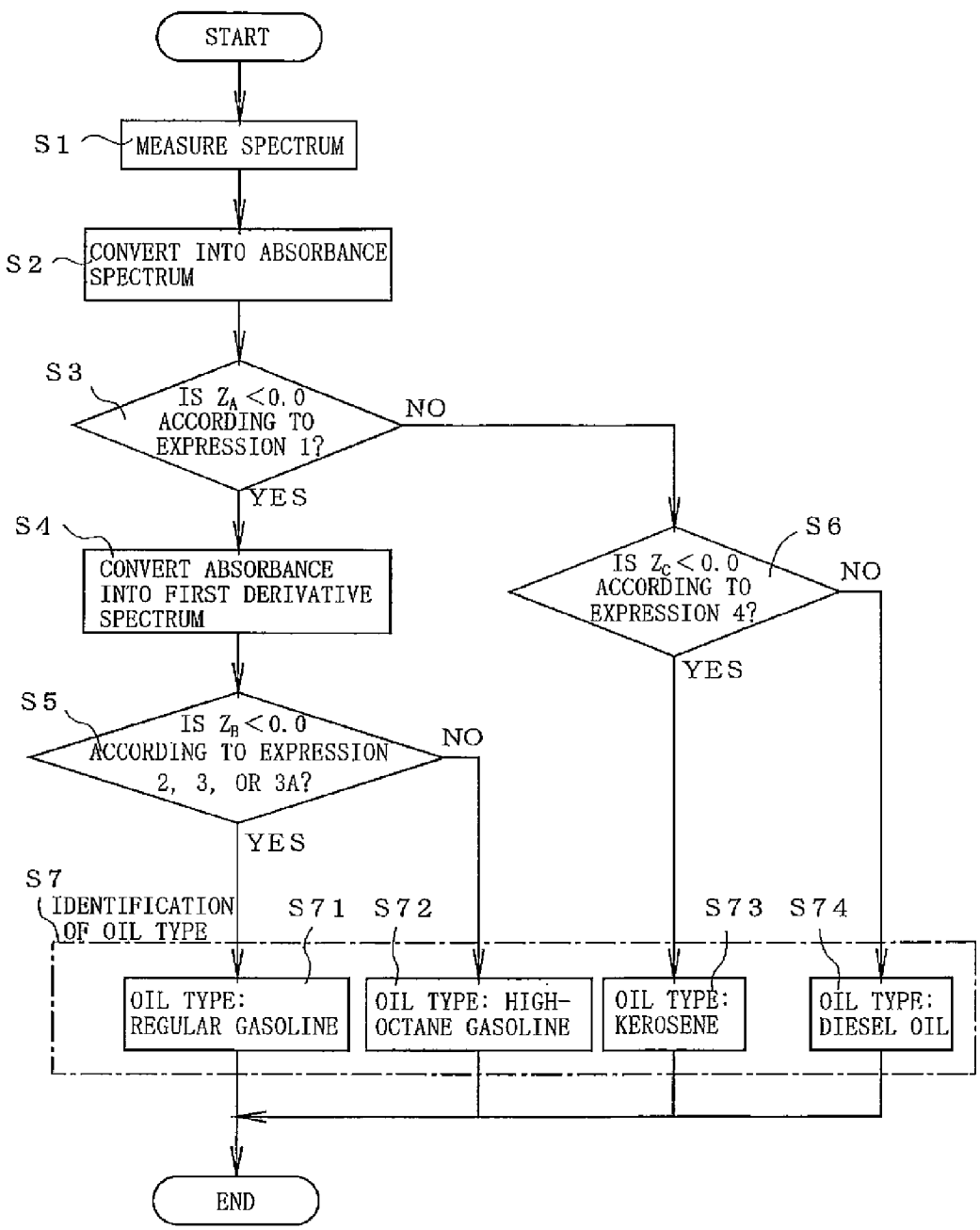
FIG. 1 is a flowchart showing an oil type discrimination method according to a first embodiment of the present invention.

FIG. 1 is a flowchart showing an oil type discrimination method according to a first embodiment of the present invention. In this method, the absorbance spectrum of a sample is found by the already known absorptiometric method using near infrared light and then the type of oil (regular gasoline, high-octane gasoline, kerosene, and diesel oil) of a sample is discriminated based on the absorbance spectrum.

Figure 2:
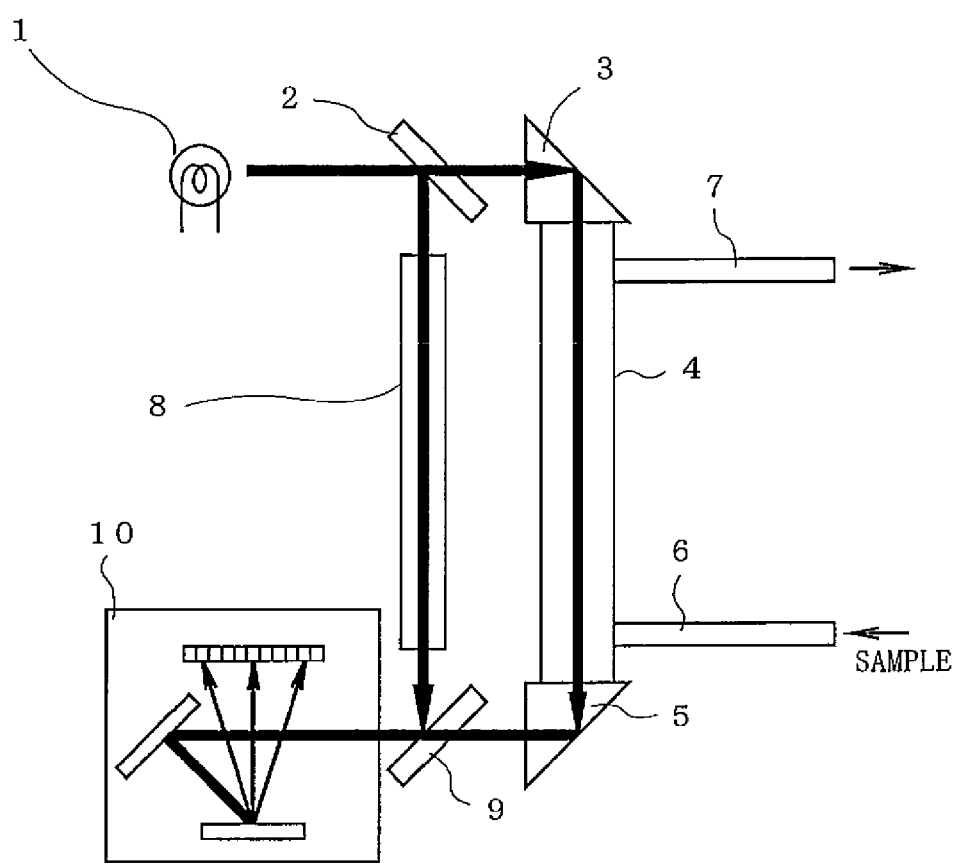
FIG. 2 is a configuration diagram of a detection cell used in each embodiment of the present invention.

The configuration of a detection cell is outlined with reference to FIG. 2. In FIG. 2, reference numeral 1 denotes a light source, such as a tungsten lamp, 2 and 9 denote a half mirror, 8 denotes a reference unit, 3 and 5 denote a prism mirror, 4 denotes a flow cell, 6 denotes a sample introduction tube, 7 denotes a sample discharge tube, and 10 denotes a spectrophotometer capable of detecting wavelengths (about 800 nm to 1,100 nm) in a near infrared region, which measures the transmitted light spectrum of a sample by introducing measurement light that has transmitted the sample (oil to be discriminated) in the flow cell 4 and the reference light that has transmitted the reference unit 8 into the spectrophotometer 10 via the half mirror 9.

The detection cell is arranged, for example, near a pipeline and used in such a manner that the oil that flows through the pipeline is introduced from the sample introduction tube 6 into the flow cell 4 and is returned to the pipeline via the sample discharge tube 7. To the detection cell, an oil type discriminator main body is attached integrally, including a signal processing circuit that processes an output signal from the spectrophotometer 10, an oil type discrimination circuit that performs various discrimination processes (described later), a setting input circuit, an output circuit, a display unit or the like and all of the components are configured as an oil type discriminator with an explosion-proof structure.

Referring back to FIG. 1, a flow of oil type discrimination in the first embodiment is explained.

First, the transmission spectrum of a sample is measured using the detection cell shown in FIG. 2 (spectrum measurement step S1). Next, the transmission spectrum is converted into an absorbance spectrum with an already known method, such as a logarithmic operation (spectrum conversion step S2).

Figure 3:
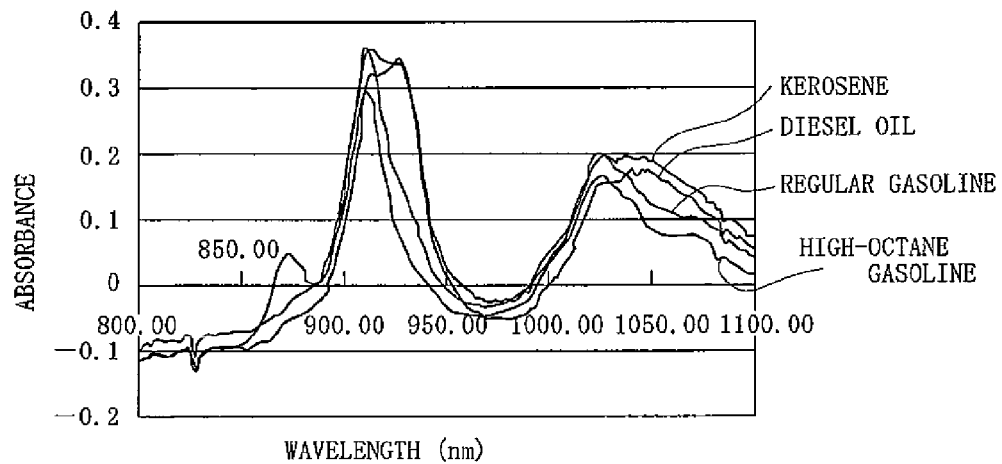
FIG. 3 shows absorbance spectra according to types of oils.

FIG. 3 shows absorbance spectra of various oils, and the respective absorbance spectra are substantially constant irrespective of the makers of oils.

Next, from the following expression 1, a value $Z_A$ is found and the value $Z_A$ is compared with the first reference value 0.0 in terms of magnitude and thus the first discrimination process is performed (first discrimination step S3).

$$Z_A = \text{Abs}(930) - \text{Abs}(907) \qquad \text{[Expression 1]}$$

where Abs(x) denotes the absorbance of a wavelength×nm. The wavelength 930 nm in the expression 1 is a wavelength in the vicinity of 928 nm, which is the attribute wavelength of the CH bond in oil or the like (absorption wavelength by the chemical bond), and 907 nm is a wavelength in the vicinity of 913 nm, which is the attribute wavelength of the CH bond of methyl group.

In the expression 1, the difference in absorbance between the two wavelengths is found and gasoline type is discriminated from non-gasoline type depending on whether the value is positive or negative. Specifically, the absorbance at 907 nm is taken as a reference value, as shown in FIG. 3. On the other hand, in contrast to this, at the other wavelength 930 nm, the absorbance is greater than the value at 907 nm described above. That is, it can been seen that the value $Z_A$ in the expression 1 is positive when the sample is the non-gasoline type, that is, kerosene or diesel oil and conversely, the value $Z_A$ is negative when the sample is the gasoline type.

In this manner, by setting one of the two wavelengths to such one so that the value of its absorbance is a reference value and the other wavelength so that there is a large difference between the values of absorbance, it is possible to find a remarkable difference in absorbance between the two wavelengths and to realize discrimination between the gasoline type and the non-gasoline type.

Accordingly, the absorbance of the attribute wavelengths 928 nm and 913 nm, at which the absorbance spectrum forms its peak, is not used to find $Z_A$ but the wavelengths 930 nm and 907 nm are selected intentionally, which are the wavelengths in the vicinities of these attribute wavelengths. This idea also applies to the wavelengths used in a third discrimination process (described later).

The first discrimination process is a process to discriminate between the gasoline type and the non-gasoline type (kerosene/diesel oil type) and when $Z_A<0.0$ (S3 YES), the type of oil is discriminated to be the gasoline type and then the process is advanced to step S4. When $Z_A \geqq 0.0$ (S3 NO), the type of oil is discriminated to be the kerosene/diesel oil type and the procedure is advanced to step S6 (described later).

Figure 4:
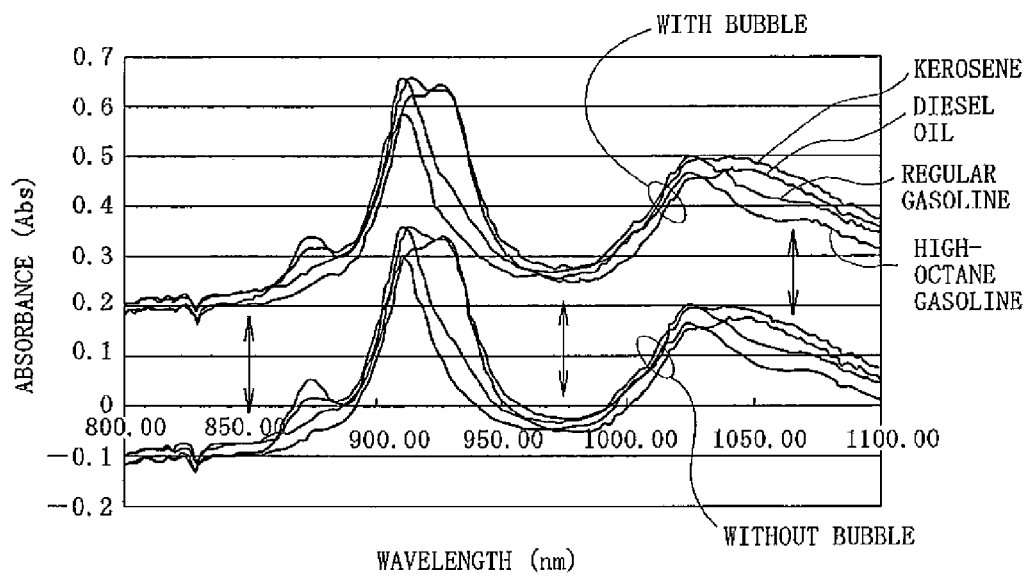
FIG. 4 shows absorbance spectra of respective types of oils according to presence of bubbles in the oils.

In the first discrimination process, discrimination is performed based on the sign (positive/negative) of the difference in absorbance between the predetermined two wavelengths, which have been found from the expression 1 and even if light-shielding components, such as bubble, water, and iron powder, exist in the oil, the absorbance only changes its absolute value as a whole and the difference in absorbance will remain unchanged. That is, FIG. 4 shows the absorbance spectra of various oils when bubbles exist and when not, and it can be seen that the difference in absorbance between the two wavelengths (for example, 930 nm and 907 nm) is substantially constant for each type of oil irrespective of the presence of bubbles.

Thus, according to the first discrimination process using the expression 1, even when there exist light-shielding components, such as bubbles, in the oil, it is possible to accurately discriminate between the gasoline type and the non-gasoline type by focusing attention on the difference in absorbance between the predetermined two wavelengths, that is, the shape of the absorbance spectrum.

Figure 5:
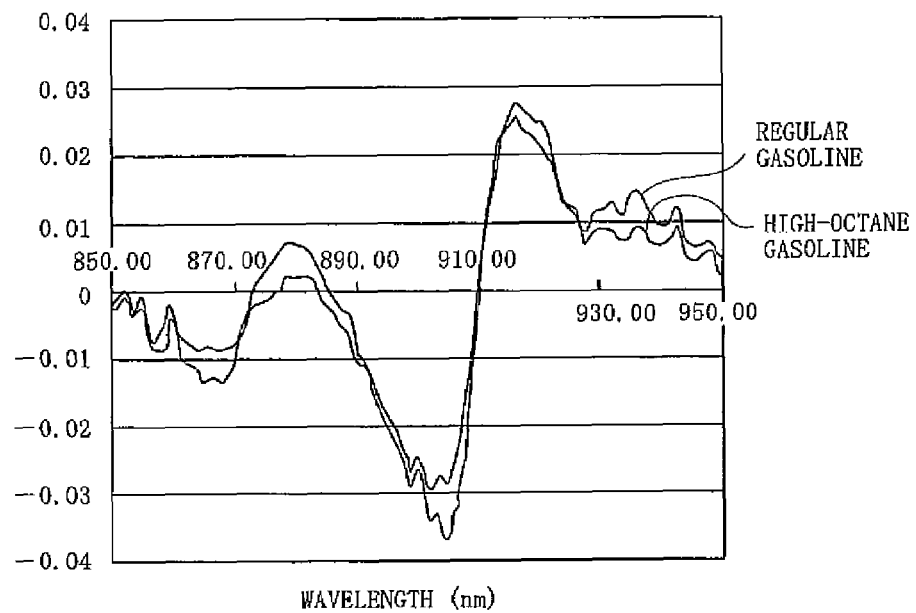
FIG. 5 shows first derivative spectra of absorbance of regular gasoline and high-octane gasoline.

When the type of oil is determined to be the gasoline type (S3 YES), in order to discriminate between regular gasoline and high-octane gasoline, the absorbance is converted into a first derivative spectrum (differential spectrum) (first derivative step S4). FIG. 5 shows the first derivative spectra of the absorbance of regular gasoline and high-octane gasoline.

The reason for the use of the first derivative spectrum of the absorbance here is that the first derivative value of the absorbance does not change even if the absorbance itself changes as a result of the presence of light-shielding components, such as bubbles, in the oil.

Next, a value $Z_B$ is found from the following expression 2 or expression 3 and the value $Z_B$ is compared with the second reference value 0.0 in terms of magnitude and thus the second discrimination process is performed (second discrimination step S5). A case that expression 3A is used in the second discrimination step S5 in FIG. 1 will be described later.

The following expression 2 is an operation expression when four wavelengths are used for the operation of the value $Z_B$, and the expression 3 is an operation expression when five wavelengths are used.

$$Z_B = \alpha_1 + \beta_1 \times 1stD\ Abs(868) + \beta_2 \times 1stD\ Abs(881) + \beta_3 \times 1stD\ Abs(930) + \beta_4 \times 1stD\ Abs(939) \quad \text{[Expression 2]}$$

$$Z_B = \alpha_{11} + \beta_{11} \times 1stD\ Abs(868) + \beta_{12} \times 1stD\ Abs(881) + \beta_{13} \times 1stD\ Abs(930) + \beta_{14} \times 1stD\ Abs(939) + \beta_{15} \times 1stD\ Abs(960) \quad \text{[Expression 3]}$$

In the expression 2 and the expression 3, $\alpha_1$ and $\alpha_{11}$ are constants, $\beta_1$ to $\beta_4$, $\beta_{11}$ to $\beta_{15}$ are coefficients, and $1stDAbs(x)$ denotes the first derivative value of the absorbance of a wavelength×nm.

Further, 868 nm is a wavelength in the vicinity of the attribute wavelength 875 nm of the aromatic CH bond, 881 nm is a wavelength in the vicinity of the attribute wavelength 875 nm of the aromatic CH bond similar to 868 nm and 930 nm is a wavelength in the vicinity of the attribute wavelength 928 nm of the CH bond of oil or the like, 939 nm is a wavelength in the vicinity of the attribute wavelength 934 nm of the CH bond of methylene group or the attribute wavelength 938 nm of the CH bond of methyl group, respectively, and 960 nm is a wavelength in the vicinity of the attribute wavelength 970 nm of the OH bond of water or the like.

In the expression 2 and the expression 3, the first derivative value of the absorbance is used and the first derivative value is zero at the attribute wavelength at which the absorbance spectrum forms its peak, and therefore, the attribute wavelength is not used basically but a wavelength in its vicinity is used in the operation of the expression 2 or the expression 3.

Further, the constants $\alpha_1$ and $\alpha_{11}$ and the coefficients $\beta_1$ to $\beta_4$ and $\beta_{11}$ to $\beta_{15}$ are determined using the determination analysis or the like, which is a multivariate analysis technique, so that the value $Z_B$ found from the expression 2 or the expression 3 will be a negative value or a positive value, the difference in the value of which between regular gasoline and high-octane gasoline is large (for example, when the expression 2 that uses four wavelengths is used, the value $Z_B$ calculated for regular gasoline is −80 and the value $Z_B$ calculated for high-octane gasoline is +80).

As a result of the assiduous study by the inventors of the present invention, the respective constant and coefficients in the expression 2 are, for example, determined as follows.

$\alpha_1 = -589.6$
$\beta_1 = 29898$
$\beta_2 = 15729.9$
$\beta_3 = -10224.1$
$\beta_4 = 8306.9$ Further, the respective constant and coefficients in the expression 3 are, for example, determined as follows.

$\alpha_{11} = -8620.46$
$\beta_{11} = -488440$
$\beta_{12} = -81631.2$
$\beta_{13} = 1144616$
$\beta_{14} = -555753$
$\beta_{15} = -1000852$ The constants $\alpha_1$ and $\alpha_{11}$ and the coefficients $\beta_1$ to $\beta_4$ and $\beta_{11}$ to $\beta_{15}$ change depending on how many wavelengths are used for which the first derivative value is found and the values of the wavelengths, and therefore, they are not determined uniquely.

In the present embodiment, four wavelengths are used in the expression 2 and five wavelengths in the expression 3, however, it is also possible to perform the second discrimination process by selecting a plurality of wavelengths from among up to seven wavelengths including additional wavelengths 906 nm and 920 nm and creating an operation expression equivalent to the expression 2 or the expression 3.

906 nm is a wavelength in the vicinity of the attribute wavelength 913 nm of the CH bond of methyl group and 920 nm is substantially an intermediate value between the attribute wavelength 913 nm of the CH bond of methyl group and the attribute wavelength 928 nm of the CH bond of oil or the like.

After $Z_B$ is found from the expression 2 or the expression 3, in the type of oil identification step S7, when $Z_B<0.0$ (S5 YES), the oil type is discriminated to be regular gasoline (S71) and when $Z_B \geqq 0.0$ (S5 NO), the type of oil is discriminated to be high-octane gasoline (S72).

On the other hand, in the step S3 described above, when $Z_A \geqq 0.0$ (S3 NO), that is, when the type of oil is discriminated to be non-gasoline type, the discrimination between kerosene and diesel oil is performed by the third discrimination process (third discrimination step S6). In the third discrimination process, a value $Z_C$ is found from the following expression 4 and the value $Z_C$ is compared with the third reference value 0.0 in terms of magnitude.

$$Z_C = Abs(930) - Abs(915) \quad \text{[Expression 4]}$$

where 915 nm is a wavelength in the vicinity of the attribute wavelength 913 nm of the CH bond of methyl group.

After the value $Z_C$ is found from the expression 4, in the oil type identification step S7, when $Z_C<0.0$ (S6 YES), the type of oil is discriminated to be kerosene (S73) and when $Z_C \geq 0.0$ (S6 NO), the type of oil is discriminated to be diesel oil (S74).

The results of the discrimination among regular gasoline, high-octane gasoline, kerosene, and diesel oil (S71 to S74) are displayed on the display unit of the oil type discriminator main body or utilized as an output to be transmitted to outside.

As described above, according to the present embodiment, it is possible to accurately discriminate between regular gasoline and high-octane gasoline and, as a matter of course, to discriminate between kerosene and diesel oil, which are of non-gasoline type, even if light-shielding components, such as bubbles, water, and iron powder, exist.

Further, by setting the wavelengths, constants, and coefficients used in the expression 2 or the expression 3 to proper values, a value can be selected as the value $Z_B$, with which value, it is possible to clearly discriminate between regular gasoline and high-octane and at the same time, to grasp a rough mixture ratio by evaluating the value $Z_B$ when regular gasoline and high-octane gasoline are mixed.

Further, when near infrared light having a long wavelength is used, in general, in a sample including water, the near infrared light is absorbed by the water and thus there is a problem that an accurate measurement is not available. In the present embodiment, however, light in a comparatively short wavelength range of the near infrared region is utilized, and therefore, the absorption of light by water is small and thus the above problems can be avoided.

When near infrared light having a long wavelength is used, it is necessary to take into consideration the use of a high-performance light source or spectrophotometer, the use of a flow cell made of a material suitable to increase transmittance (for example, calcium fluoride and zinc selenide; however, these are difficult to handle and expensive), or the provision of facilities to prevent the deliquescence of optical parts due to nitrogen purge or the like, resulting in an expensive detection cell.

In contrast thereto, when near infrared light having a short wavelength is used as in the present embodiment, it is not necessary to provide extra facilities compared to a case of the use of near infrared light having a long wavelength, and an inexpensive detection cell can be used. For example, as a material of a flow cell, anhydrous synthetic quartz, Pyrex (registered trademark) or the like, which are easier to handle and inexpensive, can be used.

In the first embodiment, in the second discrimination step S5, the value obtained from the expression 2 and the expression 3 is compared with the second reference value 0.0 and thus regular gasoline is discriminated from high-octane gasoline. However, as a result of the study further done by the inventors of the present invention, it has been revealed that a higher precision discrimination is available using a method to be described below.

That is, a value, which is obtained by multiplying respective first derivative values of absorbance of three wavelengths, that is, two wavelengths existing in the vicinities of the respective attribute wavelengths of the predetermined chemical bonds (hereinafter, "attribute wavelength group") and one wavelength, which is the attribute wavelength itself of the predetermined chemical bond (hereinafter, "specific attribute wavelength"), by respective coefficients, adding up the products, and further adding a constant to the sum, is compared with the second reference value, and thus, regular gasoline is discriminated from high-octane gasoline.

Specifically, the value $Z_B$ is found from the following expression 3A and the value $Z_B$ is compared with the second reference value 0.0 in terms of magnitude and thus the second discrimination process is performed.

$$Z_B = \alpha_{21} + \beta_{21} \times 1stD\,Abs(880) + \beta_{22} \times 1stD\,Abs(920) + \beta_{23} \times 1stD\,Abs(934) \quad \text{[Expression 3A]}$$

In the expression 3A, $\alpha_{21}$ is a constant, $\beta_{21}$ to $\beta_{23}$ are coefficients, and $1stD\,Abs(x)$ is the first derivative value of the absorbance of a wavelength×nm as before.

In the expression 3A, as two wavelengths existing in the vicinity of the attribute wavelength group, 880 nm in the vicinities of the attribute wavelength 875 nm of the aromatic CH bond and 920 nm, which is substantially an intermediate value between the attribute wavelength 913 nm of the CH bond of methyl group and the attribute wavelength 928 nm of the CH bond of oil or the like, are used. Further, as the one wavelength, which is the specific attribute wavelength, the attribute wavelength 934 nm itself of the CH bond of methyl group is used.

As a result of extensive studies by the inventors, each of the constant and coefficients in the expression 3A are, for example, determined as follows.

$\alpha_{21} = -22.4$
$\beta_{21} = -1592.6$
$\beta_{22} = -6836.7$
$\beta_{23} = 13951.8$ An oil type discrimination method according to a second embodiment of the present invention is explained next.

As described above, there is a possibility that two types of oils are mixed before and after switching between types of oils to be transported in a pipeline or at an oil tank station. Depending on the types of oils to be mixed, there is a case that their absorbance cannot be discriminated clearly from the absorbance of a single type of oil.

Figure 6:
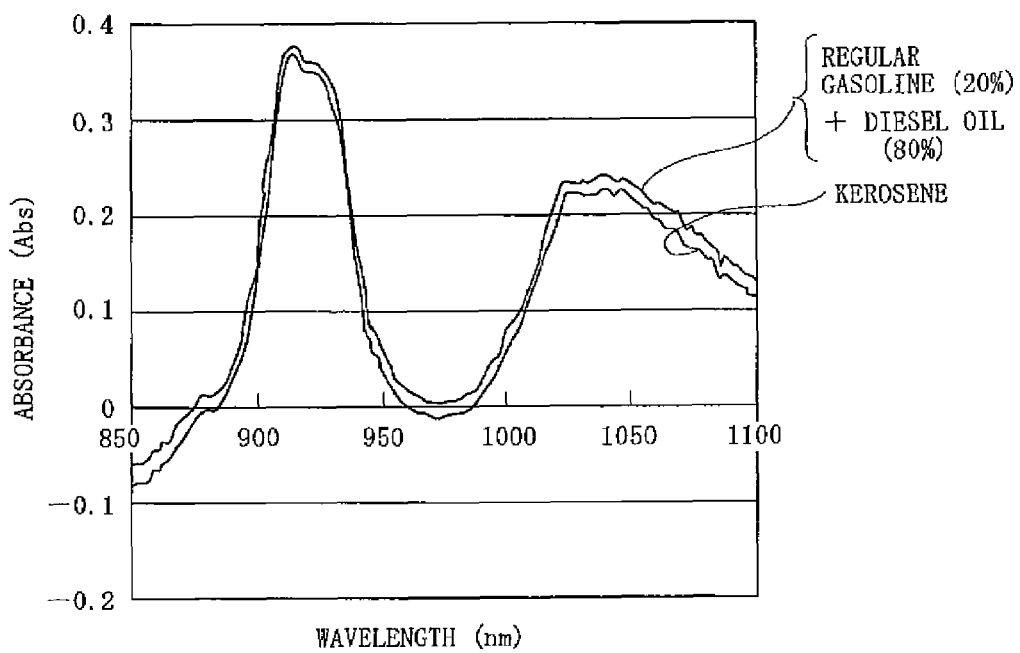
FIG. 6 shows absorbance spectra of a mixed oil and a single type of oil.

FIG. 6 shows the absorbance spectrum of a mixed oil of regular gasoline 20% and diesel oil 80% and that of kerosene, a single type of oil, the shapes of which closely resembling each other. Therefore, if discrimination is performed based on only the shapes of the absorbance spectra as in the first embodiment, there is a possibility that the type of oil is discriminated erroneously.

Accordingly in the second embodiment, as a preliminary process of the first discrimination process (first discrimination step S3) in the first embodiment, a process to determine whether the sample is a mixed oil is added.

Figure 7:
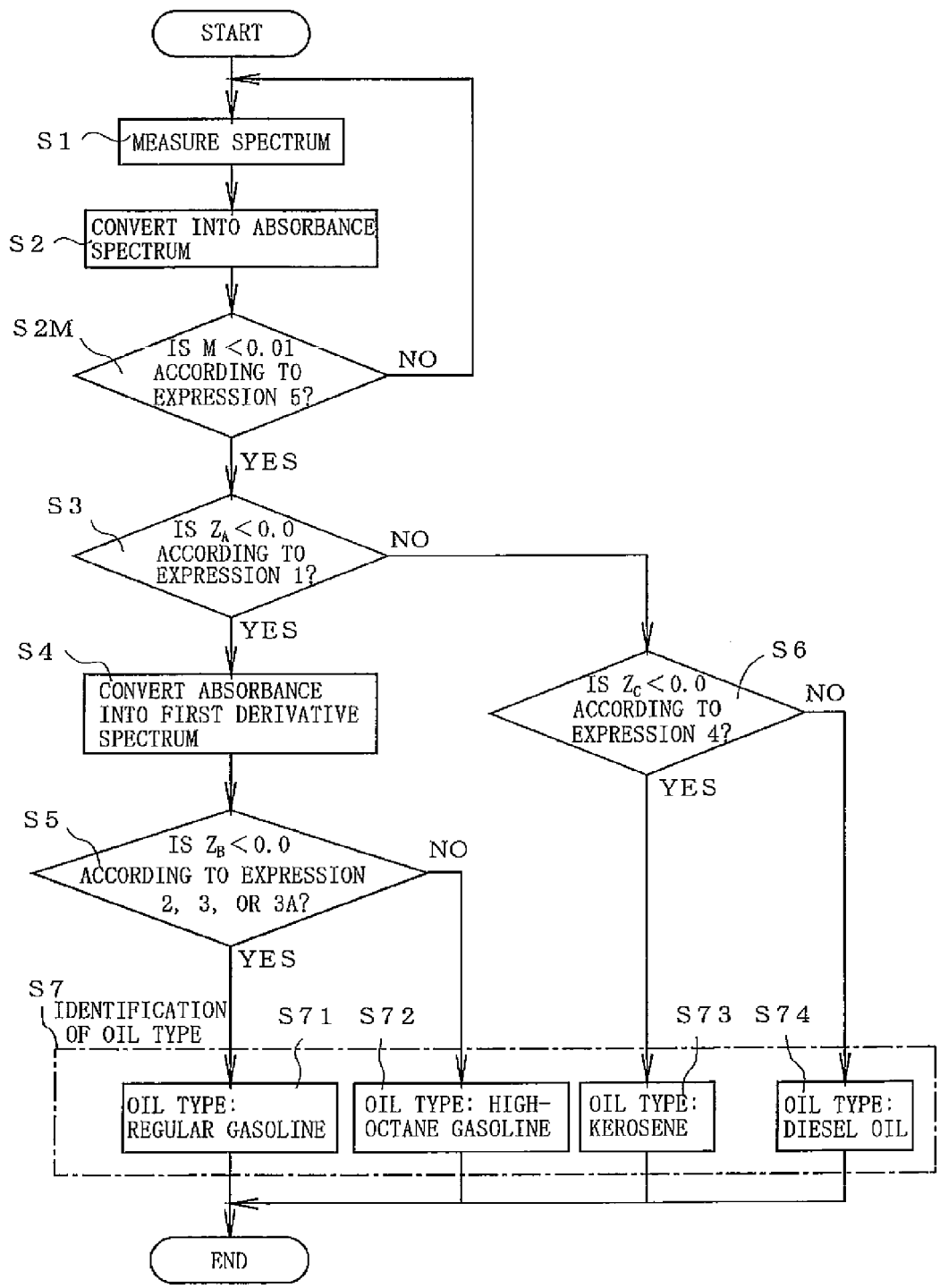
FIG. 7 is a flowchart showing an oil type discrimination method according to a second embodiment of the present invention.

FIG. 7 is a flowchart showing the second embodiment. In the second embodiment, in the previous stage of the first discrimination step S3, the process to determine whether oils are mixed (mixture determination step S2M) is added, as described above.

In this determination process, whether a value M found by the following expression 5 is smaller than a determination value (for example, a constant, such as 0.01) and determination is repeated until M becomes smaller than the determination value and after that, the procedure is advanced to the oil type discrimination process after step S3.

$$M = sqrt[\{pre\,Abs(874) - Abs(874)\}^2 + \{pre\,Abs(910) - Abs(910)\}^2 + \{pre\,Abs(928) - Abs(928)\}^2] \quad \text{[Expression 5]}$$

In the expression 5, $sqrt[y]$ is a root of y, $pre\,Abs(x)$ is a previous measurement of the absorbance of the wavelength× nm, and $Abs(x)$ is the current measurement as before.

That is, when a mixed oil does not flow constantly in a pipeline or at an oil tank station, that is, plural types of oils exist in a mixed manner, the absorbance spectrum continues to change over time. Therefore, before the oil type discrimination, when the amount of change in the absorbance spectrum becomes smaller than a determination value, it is regarded that the mixed state of types of oils is cancelled (a single type of oil), and then the procedure is advanced to the oil type discrimination process after step S3.

The expression 5 described above is based on the principle that the value M is obtained by finding the root of the sum of the differences between the previous measurement and the current measurement squared and when the value M becomes smaller than the determination value set in advance, the actual oil type discrimination is started. In the expression 5, attention is focused on the three wavelengths 874 nm, 910 nm, and 928 nm, however, the wavelengths and the number of the wavelengths should be selected appropriately depending on the types of oils that can be thought to be mixed.

According to the present embodiment, there is no possibility that the oil type discrimination is started in the state where plural types of oils are mixed and it is possible to prevent in advance the mixed oil from being discriminated erroneously to be a single type of oil the absorbance spectrum of which resembles that of the mixed oil.

In the present embodiment, the mixture determination process is performed using the previous measurement and the current measurement of the absorbance, however, the mixture determination process can be performed using the previous measurement and the current measurement of the transmission spectrum measured in step S1.

Also in the present embodiment, the expression 3A can be used besides the expression 2 and the expression 3 in the second discrimination step S5, as shown in FIG. 7.

Figure 8:
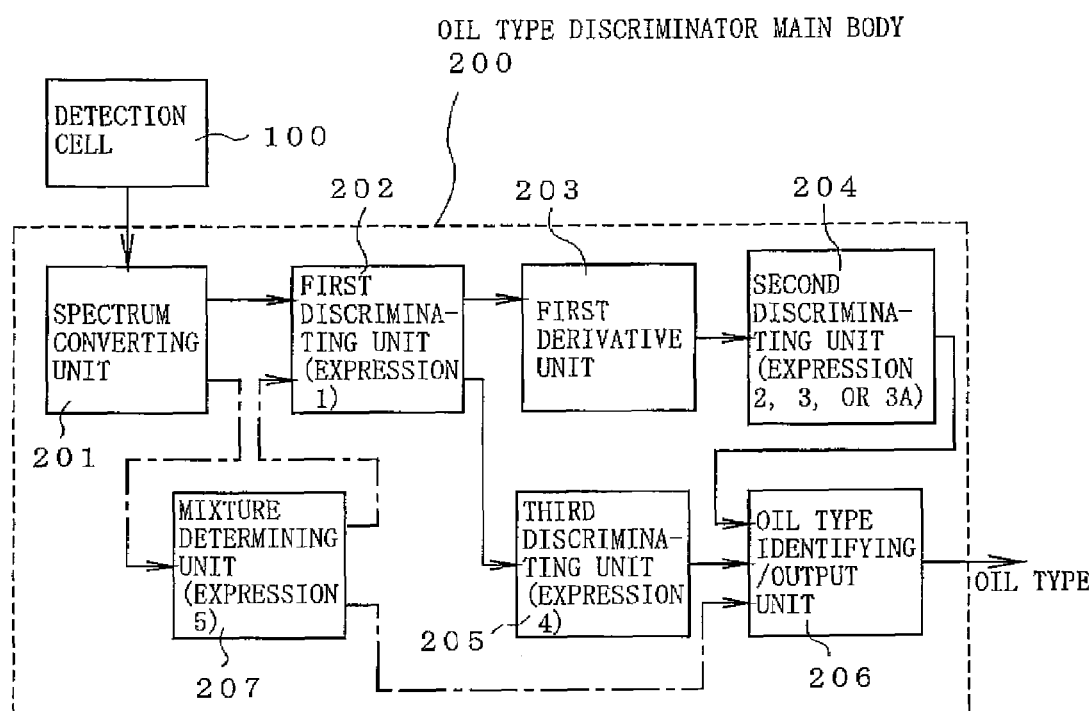
FIG. 8 is a functional block diagram showing an oil type discriminator according to another embodiment of the present invention.

FIG. 8 is a functional block diagram showing an oil type discriminator according to another embodiment of the present invention.

In FIG. 8, reference numeral 100 denotes a detection cell having the configuration as shown in FIGS. 2 and 200 denotes an oil type discriminator main body, and the main body 200 is formed into a pressure-proof and explosion-proof structure.

Reference numeral 201 is a spectrum converting unit that converts the transmission spectrum measured by the detection cell 100 into an absorbance spectrum, 202 denotes a first discriminating unit that performs the first discrimination process using the expression 1 described above, 203 is a first derivative unit that converts the absorbance into a first derivative spectrum, 204 denotes a second discriminating unit that performs the second discrimination process using the expression 2 or the expression 3 or the expression 3A, 205 denotes a third discriminating unit that performs the third discrimination process using the expression 4, and 206 denotes an oil type identifying/output unit that identifies the type of oil from the discrimination results by the respective discriminating units 204 and 205 and executes display output, warning output, transmission output or the like.

When the flow in FIG. 7 explained above as the second embodiment of the oil type discrimination method is executed, a mixture determining unit 207 provided between the spectrum converting unit 201 and the first discriminating unit 202 determines whether plural types of oils are mixed using the expression 5. When it is determined that plural types of oils are not mixed, the procedure is advanced to the normal oil type discrimination process after that of the first discriminating unit 202 and when determined to be mixed, a mixture determination signal is sent to the oil type identifying/output unit 206 to cause it to execute warning output or the like.

Each unit of the oil type discriminator main body 200 described above is implemented by an operation processing device as hardware including a CPU, a memory or the like, and a program as software in the memory and the program is configured so as to execute the flow in FIG. 1 or FIG. 7 described above. The oil type discriminator main body 200 also includes programs and circuits that control in sequence each operation of the initialization of the oil type discriminator, various settings, correction, alarm output, transmission output or the like, however, these are not shown in the drawings for convenience.

The wavelengths used in the expressions 1, 2, 3, 3A, 4, and 5 in each embodiment described above are only illustrative and an idea that a wavelength in the vicinity of an attribute wavelength corresponding to a specific chemical bond of each type of fuel oil is used to perform the first to third discrimination processes and, if necessary, whether plural types of oils are mixed is determined should be included in the oil type discrimination method or the oil type discriminator according to the present invention.

The invention claimed is:

1. An oil type discrimination method, in which a sample, which is an oil to be discriminated from another, is irradiated with near infrared light and a type of oil of the sample is discriminated by measuring absorbance of a specific wavelength of the near infrared light, the method comprising:
   a spectrum measurement step of measuring a transmission spectrum of the near infrared light that has transmitted the sample;
   a spectrum conversion step of converting the transmission spectrum into an absorbance spectrum;
   a first discrimination step of finding a difference in absorbance between two wavelengths existing in the vicinities of respective attribute wavelengths of predetermined chemical bonds and discriminating whether the sample is gasoline type or non-gasoline type by comparing the difference in absorbance with a first reference value;
   a first derivative step of converting the absorbance into a first derivative spectrum when the sample is discriminated to be the gasoline type in the first discrimination step;
   a second discrimination step of discriminating whether the sample is regular gasoline or high-octane gasoline by comparing a value, which is obtained by multiplying respective first derivative values of absorbance of at least four wavelengths existing in the vicinities of the respective attribute wavelengths of the predetermined chemical bonds by respective coefficients, adding up products, and further adding a constant to a sum, with a second reference; and
   a third discrimination step of discriminating whether the sample is kerosene or diesel oil by finding the difference in absorbance between two wavelengths existing in the vicinities of the respective attribute wavelengths of the predetermined chemical bonds and comparing the difference in absorbance with a third reference value when the sample is discriminated to be the non-gasoline type in the first discrimination step.

2. The oil type discrimination method according to claim 1, wherein the attribute wavelengths in the second discrimination step are 875 nm, 928 nm, and 934 nm or 938 nm.

3. The oil type discrimination method according to claim 1, wherein the attribute wavelengths in the second discrimination step are 875 nm, 928 nm, 970 nm, and 934 nm or 938 nm.

4. An oil type discrimination method, in Which a sample, which is an oil to be discriminated from another, is irradiated with near infrared light and a type of oil of the sample is discriminated by measuring absorbance of a specific wavelength of the near infrared light, the method comprising:

a spectrum measurement step of measuring a transmission spectrum of the near infrared light that has transmitted the sample;

a spectrum conversion step of converting the transmission spectrum into an absorbance spectrum;

a first discrimination step of finding a difference in absorbance between two wavelengths existing in the vicinities of respective attribute wavelengths of predetermined chemical bonds and discriminating whether the sample is gasoline type or non-gasoline type by comparing the difference in absorbance with a first reference value;

a first derivative step of converting the absorbance into a first derivative spectrum when the sample is discriminated to be the gasoline type in the first discrimination step;

a second discrimination step of discriminating whether the sample is regular gasoline or high-octane gasoline by comparing a value, which is obtained by multiplying respective first derivative values of three wavelengths, that is, two wavelengths existing in the vicinities of the respective attribute wavelengths (an attribute wavelength group) of the predetermined chemical bonds and one wavelength of the attribute wavelength itself (a specific attribute wavelength) of the predetermined chemical bond, by respective coefficients, adding up products, and further adding a constant to a sum, with a second reference; and a third discrimination step of discriminating whether the sample is kerosene or diesel oil by finding the difference in absorbance between two wavelengths existing in the vicinities of the respective attribute wavelengths of the predetermined chemical bonds and comparing the difference in absorbance with a third reference value when the sample is discriminated to be the non-gasoline type in the first discrimination step.

5. The oil type discrimination method according to claim 4, wherein the wavelengths of the attribute wavelength group in the second discrimination step are 875 nm, and 913 nm or 928 nm, and the specific attribute wavelength is 934 nm.

6. The oil type discrimination method according to any one of claims 1 to 5, wherein prior to the first discrimination step, a mixture determination step of determining whether a deviation of the absorbance spectrum or the transmission spectrum between a previous measurement and a current measurement is smaller than a determination value is provided, and when it is determined that the deviation is smaller than the determination value in the mixture determination step, the sample is regarded to include only one type of oil and a procedure is advanced to processing in the first discrimination step and subsequent steps.

7. An oil type discriminator comprising a detection cell that irradiates a sample, which is an oil to be discriminated, with near infrared light and measures a transmission spectrum of the near infrared light that has transmitted the sample and an oil type discriminator main body that detects absorbance of a specific wavelength from the transmission spectrum and discriminates a type of oil of the sample, wherein the oil type discriminator main body comprises:

a spectrum converting unit that converts the transmission spectrum into an absorbance spectrum;

a first discriminating unit that discriminates whether the sample is gasoline type or non-gasoline type by finding a difference in absorbance between two wavelengths existing in the vicinities of respective attribute wavelengths of predetermined chemical bonds and comparing the difference in absorbance with a first reference value;

a first derivative unit that converts the absorbance of the sample discriminated to be the gasoline type by the first discriminating unit into a first derivative spectrum;

a second discriminating unit that determines whether the sample is regular gasoline or high-octane gasoline by comparing a value including first derivative values of absorbance of at least four wavelengths existing in the vicinities of the respective attribute wavelengths of the predetermined chemical bonds with a second reference value; and a third discriminating unit that finds the difference in absorbance between two wavelengths existing in the vicinities of the respective attribute wavelengths of the predetermined chemical bonds for the sample discriminated to be the non-gasoline type by the first discriminating unit and discriminates whether the sample is kerosene or diesel oil by comparing the difference in absorbance with a third reference value.

8. An oil type discriminator comprising a detection cell that irradiates a sample, which is an oil to be discriminated, with near infrared light and measures a transmission spectrum of the near infrared light that has transmitted the sample and an oil type discriminator main body that detects absorbance of a specific wavelength from the transmission spectrum and discriminates a type of oil of the sample, wherein the oil type discriminator main body comprises:

a spectrum converting unit that converts the transmission spectrum into an absorbance spectrum;

a first discriminating unit that discriminates whether the sample is gasoline type or non-gasoline type by finding a difference in absorbance between two wavelengths existing in the vicinities of the respective attribute wavelengths of the predetermined chemical bonds and comparing the difference in absorbance with a first reference value;

a first derivative unit that converts the absorbance of the sample discriminated to be the gasoline type by the first discriminating unit into a first derivative spectrum;

a second discriminating unit that determines whether the sample is regular gasoline or high-octane gasoline by comparing a value including first derivative values of the absorbance of three wavelengths, that is, two wavelengths existing in the vicinities of the respective attribute wavelengths of the predetermined chemical bonds and one wavelength of the attribute wavelength itself of the predetermined chemical bond with a second reference value; and a third discriminating unit that finds the difference in absorbance between two wavelengths existing in the vicinities of the respective attribute wavelengths of the predetermined chemical bonds for the sample discriminated to be the non-gasoline type by the first discriminating unit and discriminates whether the sample is kerosene or diesel oil by comparing the difference in absorbance with a third reference value.

9. The oil type discriminator according to claim 7 or 8, comprising a mixture determining unit that determines whether deviation of the absorbance spectrum or the transmission spectrum between a previous measurement and a current measurement is smaller than a determination value, wherein processing by the first discriminating unit is executed by determination output from the mixture determining unit.

* * * * *